United States Patent
Sudell

(10) Patent No.: US 10,307,284 B2
(45) Date of Patent: *Jun. 4, 2019

(54) PORTABLE TRACTION DEVICE WITH SLING

(71) Applicant: THE NECK HAMMOCK, INC., Wilmington, DE (US)

(72) Inventor: Steven Sudell, Santa Monica, CA (US)

(73) Assignee: THE NECK HAMMOCK, INC., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/008,247

(22) Filed: Jun. 14, 2018

(65) Prior Publication Data

US 2018/0289525 A1    Oct. 11, 2018

Related U.S. Application Data

(63) Continuation of application No. 15/600,901, filed on May 22, 2017.

(60) Provisional application No. 62/374,259, filed on Aug. 12, 2016.

(51) Int. Cl.
*A61F 5/00* (2006.01)
*A61F 5/055* (2006.01)
*A61F 5/042* (2006.01)
*A61H 1/02* (2006.01)
*A61F 5/048* (2006.01)

(52) U.S. Cl.
CPC ............. *A61F 5/055* (2013.01); *A61F 5/042* (2013.01); *A61H 1/0218* (2013.01); *A61F 5/048* (2013.01); *A61H 2201/0123* (2013.01); *A61H 2201/1611* (2013.01)

(58) Field of Classification Search
CPC .. A61F 5/055; A61F 5/024; A61H 2201/1607
USPC ................................................ 602/35–36, 18
See application file for complete search history.

(56) References Cited

U.S. PATENT DOCUMENTS

| | | | |
|---|---|---|---|
| 2,674,996 A | 4/1954 | Stowell et al. | |
| 3,033,198 A | 5/1962 | Jensen | |
| 3,118,443 A | 1/1964 | Dykinga | |
| 3,221,735 A * | 12/1965 | Goodman | ................ A61H 1/00 602/33 |
| D213,478 S | 3/1969 | Nightingale | |
| 4,220,147 A | 9/1980 | Allen | |
| D332,495 S | 1/1993 | Lake | |

(Continued)

FOREIGN PATENT DOCUMENTS

GB         1315519 A  *  5/1973  ........... A61H 1/0218

OTHER PUBLICATIONS

International Search Report and Written Opinion issued in PCT/US2018/015415 dated Mar. 22, 2018.

(Continued)

*Primary Examiner* — Kim M Lewis
(74) *Attorney, Agent, or Firm* — Workman Nydegger

(57) ABSTRACT

A sling of a portable traction device cradles a user's head and includes a pair of shock cords attached at opposite ends of the sling. The ends of the shock cords opposite shock cords are anchored is anchored to a structure, such as a closed door at the hinged side of the door, between the door and door frame, using an anchor, at a height, to generate a tension vector at an acute angle relative to the floor. The tension applies cervical traction.

18 Claims, 11 Drawing Sheets

(56) References Cited

U.S. PATENT DOCUMENTS

| | | | |
|---|---|---|---|
| 5,451,202 A * | 9/1995 | Miller | A61H 1/0218 |
| | | | 602/35 |
| 5,479,667 A | 1/1996 | Nelson et al. | |
| D422,710 S | 4/2000 | Maynard | |
| 6,113,564 A * | 9/2000 | McGuire | A61H 1/0229 |
| | | | 482/131 |
| 6,183,501 B1 | 2/2001 | Latham | |
| 6,939,269 B2 | 9/2005 | Makofsky | |
| D550,847 S | 9/2007 | Kixmiller | |
| D626,244 S | 10/2010 | Sagnip | |
| 8,657,774 B1 | 2/2014 | Fisher | |
| 8,782,831 B2 | 7/2014 | Houston | |
| D713,049 S | 9/2014 | Shah | |
| D713,535 S | 9/2014 | Chiang et al. | |
| D749,230 S | 2/2016 | Safko | |
| 9,526,965 B2 * | 12/2016 | Gatherer | A63B 71/0054 |
| D784,546 S | 4/2017 | Gordon | |
| D789,546 S | 6/2017 | Matfus | |
| D790,072 S | 6/2017 | Hiebert | |
| 9,668,906 B2 | 6/2017 | Thorsteindottir | |
| 9,713,546 B2 | 7/2017 | Thorsteindottir | |
| D794,809 S | 8/2017 | Gramza | |
| D812,236 S | 3/2018 | Burke | |
| 2005/0113728 A1 * | 5/2005 | Heinz | A61F 5/055 |
| | | | 602/18 |
| 2006/0288490 A1 | 12/2006 | Mikkelsen et al. | |
| 2010/0222729 A1 | 9/2010 | Chin et al. | |
| 2014/0249461 A1 * | 9/2014 | Bissell | A61H 1/0218 |
| | | | 602/36 |
| 2018/0028389 A1 * | 2/2018 | Adimari | A61H 1/0292 |
| 2018/0042757 A1 | 2/2018 | Sudell | |

OTHER PUBLICATIONS

Selenechen Hammock for Neck, Neck Massager for Men Women, Relaxation Massager Great for Neck Pain Relief Amazon.
U.S. Appl. No. 29/640,156, Apr. 12, 2018, Office Action.

* cited by examiner

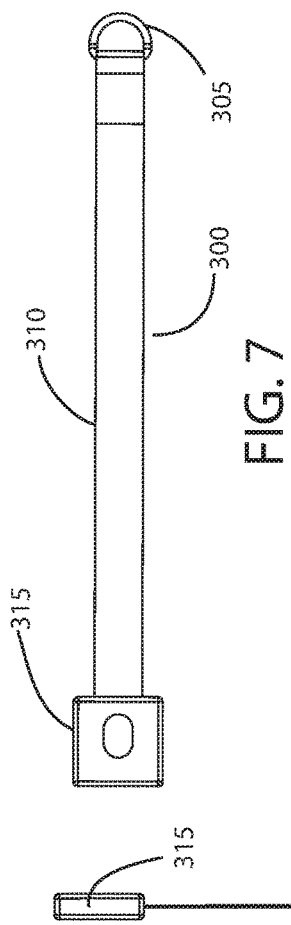
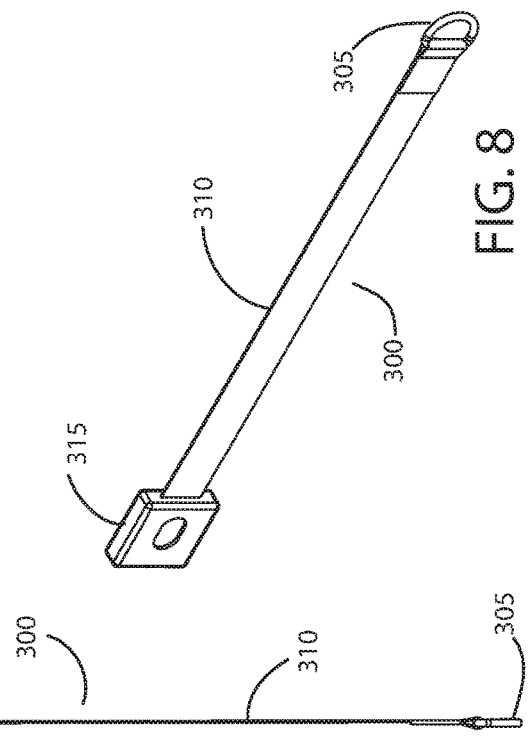
FIG. 7
FIG. 8
FIG. 9

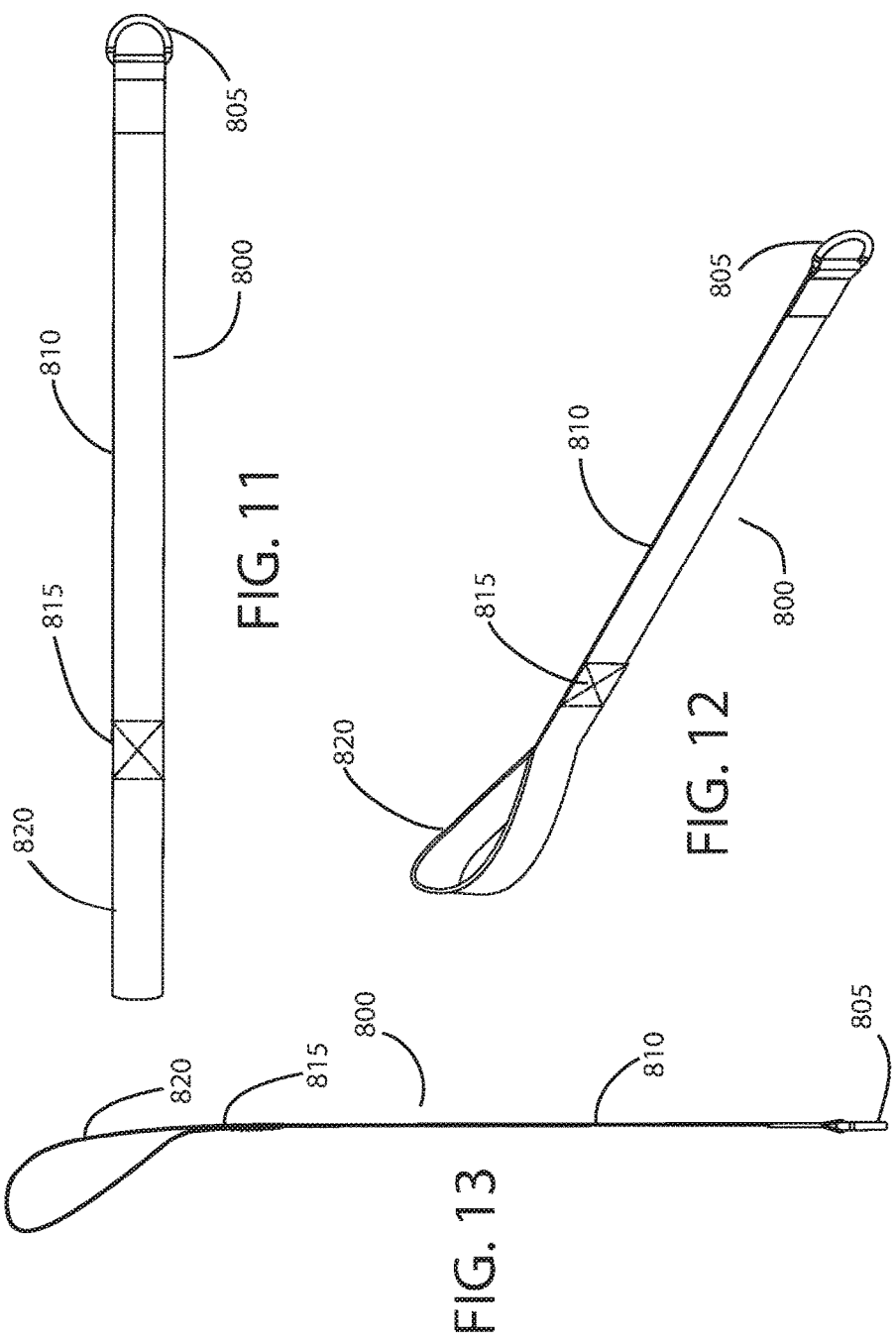

PORTABLE TRACTION DEVICE WITH SLING

RELATED APPLICATION

This application is a continuation of U.S. patent application Ser. No. 15/600,901 filed on May 22, 2017, entitled "PORTABLE TRACTION DEVICE WITH SLING", which claims the benefit of priority of U.S. Provisional Application 62/374,259 filed on Aug. 12, 2016, entitled "PORTABLE TRACTION DEVICE WITH SLING".

FIELD OF THE INVENTION

This invention relates generally to cervical traction, and, more particularly, to a portable device to apply cervical traction.

BACKGROUND

Cervical traction is a method of applying force to relieve neck pain for individuals suffering from neck arthritis, a herniated/bulging disc in the neck, pinched nerves, neck strains and cervical muscle spasms. Cervical traction entails urging the head away from the neck. Doing so, gradually stretches muscles and ligaments around the vertebrae of the spine and expands space between vertebrae. Pinched nerves are released. Herniated and bulging discs relax as pressure is relieved. Blood circulation improves to the structures of the cervical spine, helping to oxygenate muscles, nerves, tendons and ligaments.

In the past, individuals were relegated to visiting a physical therapist for neck traction. Such visits are time consuming, often inconvenient and costly. Additionally, patients can afford such visits only periodically.

Today, home cervical traction devices are legion. Using such a device, an individual apply traction effectively, conveniently and frequently. Unfortunately, however, many of the devices are complex, cumbersome, bulky, costly and potentially injurious.

As one example, many home traction devices include headgear which include straps around the user's forehead head and chin. Such headgear is not only cumbersome, constricting and inconvenient, but may also exert stresses at the jaw that may lead to or exacerbate temporomandibular disorders. As another example, many such devices require weights and pulleys to exert tension. Such devices are bulky, cumbersome and inconvenient. As yet another example, many devices include clamps and brackets for attachment to doors and furniture. Such hardware mars surface finishes and interferes with use of the door or furniture.

What is needed is an easy to use, compact, non-marring, effective traction device that minimizes discomfort and avoids potentially injurious stresses.

The invention is directed to overcoming one or more of the problems and solving one or more of the needs as set forth above.

SUMMARY OF THE INVENTION

To solve one or more of the problems set forth above, in an exemplary implementation of the invention, a portable traction device according to principles of the invention includes a sling assembly. The sling assembly includes a sling made of or including flexible material and having a first side, a second side opposite the first side, a superior edge, and an inferior edge. The sling can be elongated and sized to cradle and engage an occipital bone portion of a user's head via at least a frictional portion of the sling disposed between the superior edge and the inferior edge of the sling when the first side extends to a first side of the user's head and the second side extends to a second side of the user's head. The sling assembly can also include a base cushion attached to the sling between the superior edge and the inferior edge and approximately centered between the first and second sides of the sling, a first side cushion disposed between the base cushion and the first side of the sling, and a second side cushion disposed between the base cushion and the second side of the sling. The sling assembly can also include a pair of side attachments that include a first side attachment extending from the first side of the sling and a second side attachment extending from the second side of the sling. The portable traction device can additionally include flexible elastic tethers operable to selectively attach to the pair of side attachments via first ends of the flexible elastic tethers and an anchor operable to selectively attach to the sling and to an anchoring object.

Embodiments of the present disclosure additionally include methods of applying cervical traction to a user using the exemplary portable traction device. An exemplary method includes steps of attaching the anchor to the anchoring object, at a height above the floor; stretching the pair of flexible elastic tethers at an acute angle relative to the floor to produce a tensile force including a vector component parallel to the floor towards the anchor, and a vector component perpendicular to the floor and upward; and cradling, with the sling, while the pair of flexible elastic tethers is stretched, the head of the user, the user being substantially supine on a floor, with the user's head spaced apart from and aimed towards the anchoring object, and the user's feet aimed away from the anchoring object. The height above the floor can be about at least two feet. Additionally, the tensile force can be at least five pounds.

A portable traction device according to principles of the invention thus provides an easy to use, compact, portable, stowable, non-marring, effective traction device that minimizes discomfort and avoids potentially injurious stresses.

BRIEF DESCRIPTION OF THE DRAWINGS

The foregoing and other aspects, objects, features and advantages of the invention will become better understood with reference to the following description, appended claims, and accompanying drawings, where:

FIG. 7 is a plan view of a door anchor for a traction device according to principles of the invention; and FIG. 8 is a top perspective view of a door anchor for a traction device according to principles of the invention; and FIG. 9 is a side view of a door anchor for a traction device according to principles of the invention.

FIG. 11 is a plan view of an alternative anchor for a traction device according to principles of the invention; and FIG. 12 is a top perspective view of an alternative anchor for a traction device according to principles of the invention; and FIG. 13 is a side view of an alternative anchor for a traction device according to principles of the invention.

Those skilled in the art will appreciate that the figures are not intended to be drawn to any particular scale; nor are the figures intended to illustrate every embodiment of the invention. The invention is not limited to the exemplary embodiments depicted in the figures or the specific components, configurations, shapes, relative sizes, ornamental aspects or proportions as shown in the figures.

DETAILED DESCRIPTION

A portable traction device according to principles of the invention provides an easy to use, compact, non-marring, effective traction device that minimizes discomfort and avoids potentially injurious stresses. A sling cradles a user's head, particularly the occipital bone portion of the user's head situated at the back and lower part of the skull. The sling includes cushions for comfort and enhanced frictional engagement of the user's head. The sling also includes an arched portion that extends beyond the occipital bone portion of the user's head to the lambdoid suture and lateral portion of the parietal bones of the user's head. The sling is attached to one end of each of a pair of shock cords. The other end of each of the pair of shock cords is anchored to a fixed or immovable object (i.e., an anchoring object) such as a closed door at the hinged side of the door, between the door and door frame, using a door anchor. The door anchor is positioned at a height near the middle of the door. Tension exerted by the shock cords is directed from the cradled portion of the user's head to the anchor, at an acute angle relative to a horizontal floor surface. Thus the tensile force vector includes a horizontal component away from the user's head towards the door, and a vertical component upwardly from the floor. The upward component helps to ensure that the sling does not slip off and disengage the user's head. The invention is not limited to attachment to a door. Other elevated structures such as furniture, including table legs, may be used for anchoring.

Figure 1:
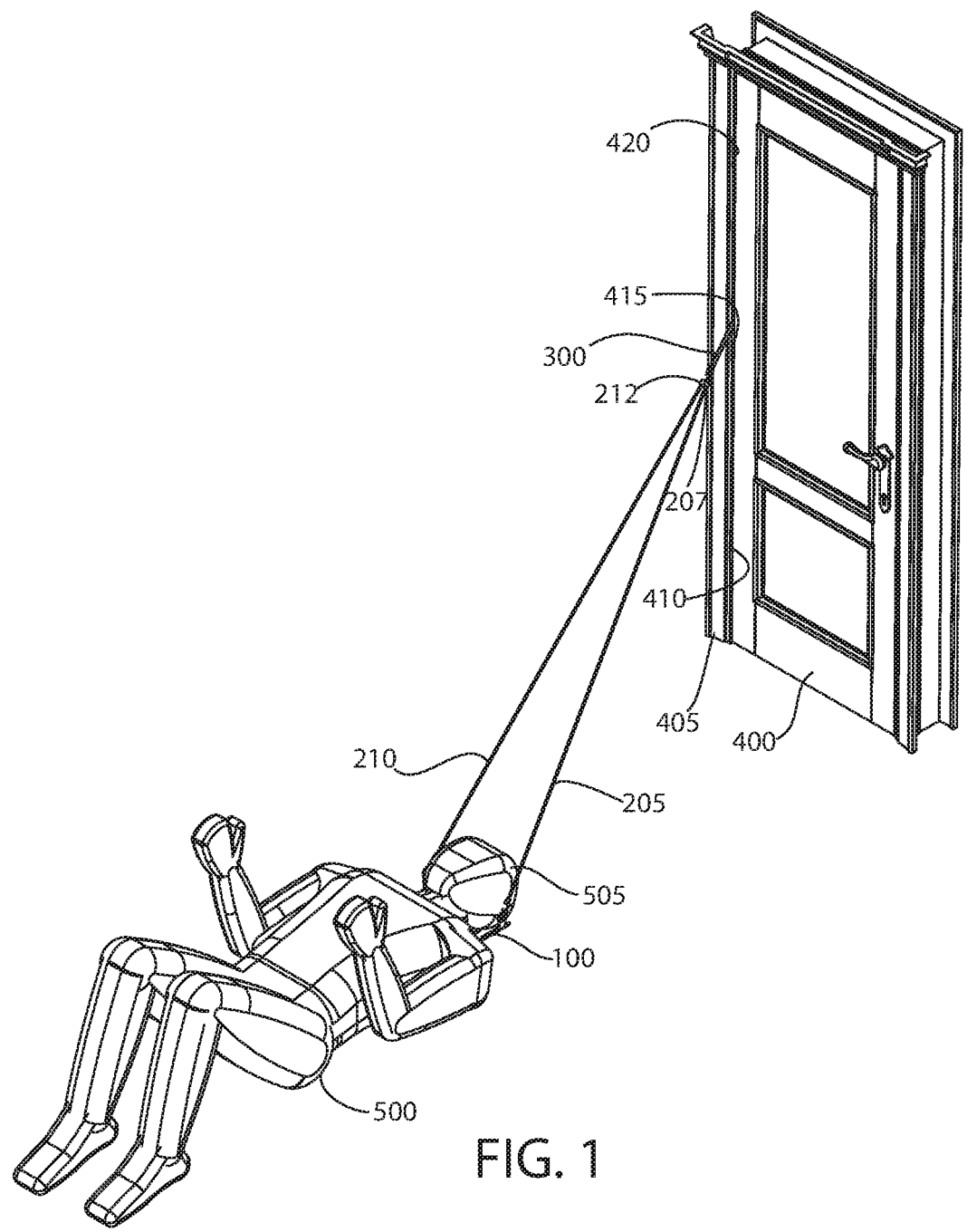
FIG. 1 is a top perspective view that conceptually illustrates a traction device in use according to principles of the invention.
Figure 2:
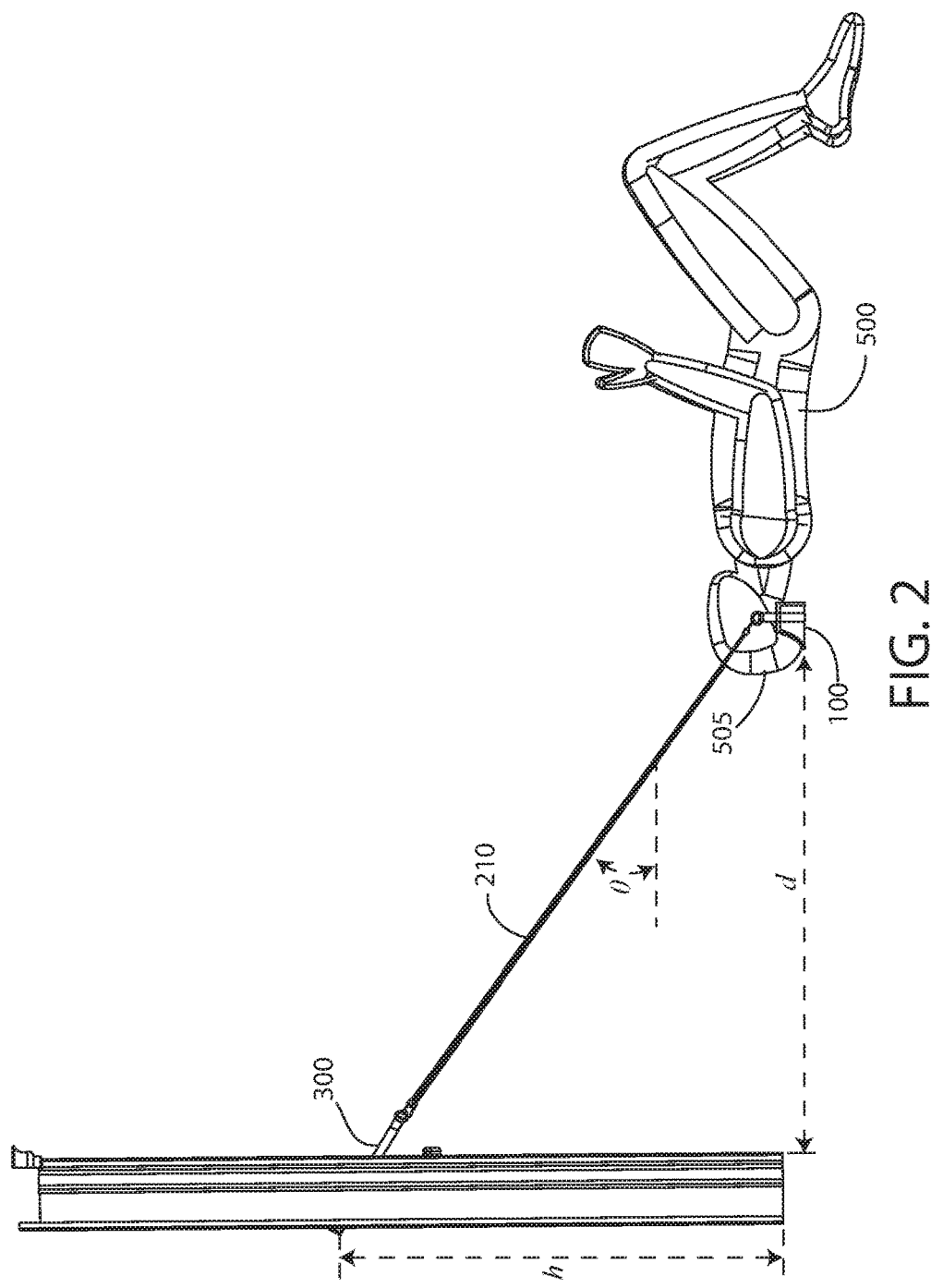
FIG. 2 is a side view that conceptually illustrates a traction device in use according to principles of the invention.
Figure 3:
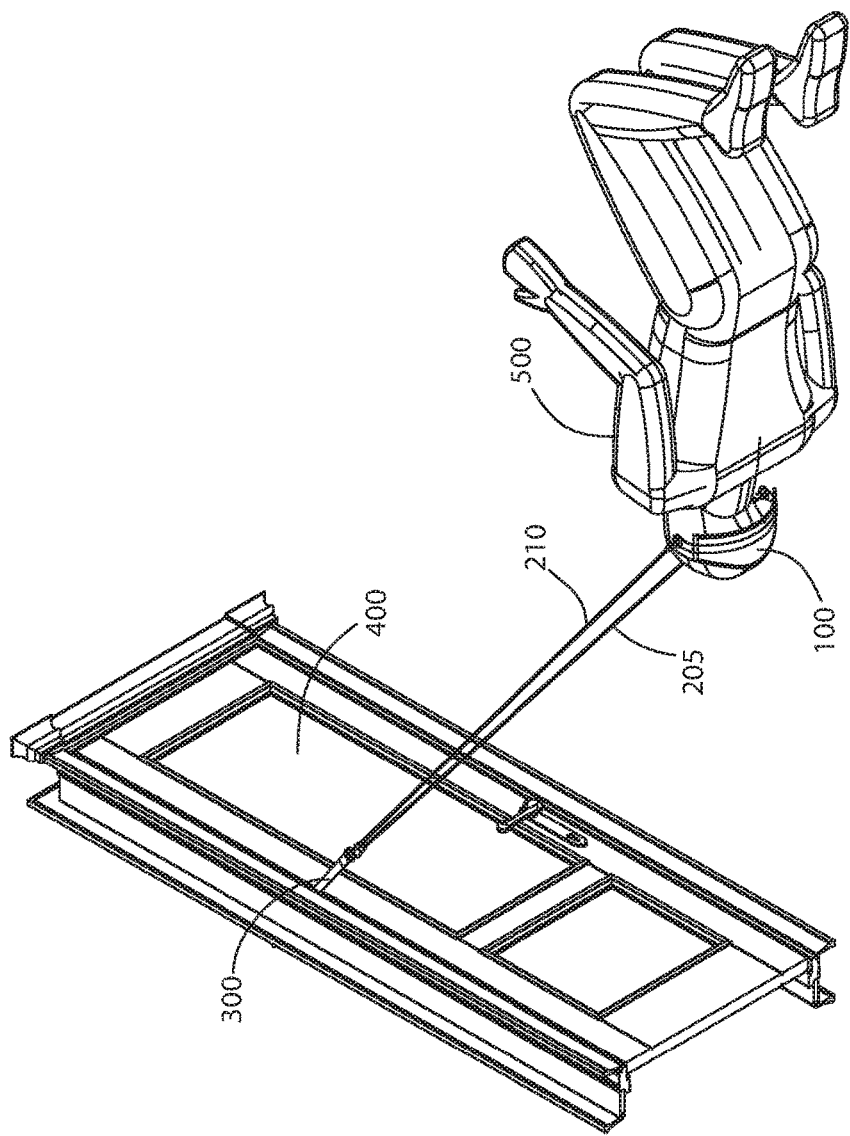
FIG. 3 is a bottom perspective view that conceptually illustrates a traction device in use according to principles of the invention.

Referring to FIGS. 1 through 3 a traction device in use according to principles of the invention is conceptually illustrated. A sling assembly 100, which is described in greater detail below with reference to FIGS. 4 and 5, cradles a user's 500 head 505, particularly the occipital bone portion of the user's head situated at the back and lower part of the skull. The sling assembly 100 extends beyond the occipital bone portion of the user's head to the lambdoid suture and lateral portion of the parietal bones of the user's head. Each of a plurality (e.g., an even number) of shock cords 205, 210 is attached at one end to the sling assembly, and at the opposite end 207, 212 to a door anchor 300, where the ends 207, 212 converge. The door anchor 300 is described in greater detail below with reference to FIGS. 7 through 9. The door anchor 300 is locked between the hinged edge of the door 400 and the door frame 405, when the door 400 is closed. In such an embodiment, the closed door is deemed an anchoring object while the sling assembly 100 is in use.

With reference to FIG. 2, net tension exerted by the shock cords 205, 210 is directed from the cradled portion of the user's head 505 to the anchor 300, at an acute angle θ (greater than 0° but less than 90°, preferably between 15° and 60°) relative to a planar (e.g., horizontal floor) surface. Thus the tensile force vector includes a horizontal component away from the user's head 505 towards the door 400, and a vertical component upwardly from the floor. The vertical component helps to ensure that the sling 100 does not slip off and disengage the user's head 505. The vertical component of the tensile force and friction between the user's head and the sling assembly 100 obviate need for a chin strap or other cumbersome head attachment. A portion of the sling 100 that cradles the user's head, particularly at the occipital bone portion of the user's head situated at the back and lower part of the skull, is a frictionally engaging portion that does not slide off the head during normal use. During normal use, the sling assembly 100 will not slide out from beneath the user's head 505. The angle θ and horizontal and vertical components of the force vector may be varied by adjusting d, the distance from the door, and h, the height of the anchor.

While the Figures may illustrate the user's head against (or nearly against) the floor, it is understood that the vertical component of the tensile force may pull the user's head upward from the floor. Such lifting of the user's head 505 provides considerable comfort to the user without appreciably compromising the horizontal component of the tensile force. A user may counteract the lifting force by urging his or her head against the floor. However, such counteraction is unnecessary.

In the bottom-up perspective view of FIG. 3, the sling assembly 100 relative to the head 505 is more clearly illustrated. The sling assembly 100 cradles the user's 500 head 505, particularly the occipital bone portion of the user's head situated at the back and lower part of the skull. The sling assembly 100 extends beyond the occipital bone portion of the user's head to the lambdoid suture and lateral portion of the parietal bones of the user's head.

Figure 10:
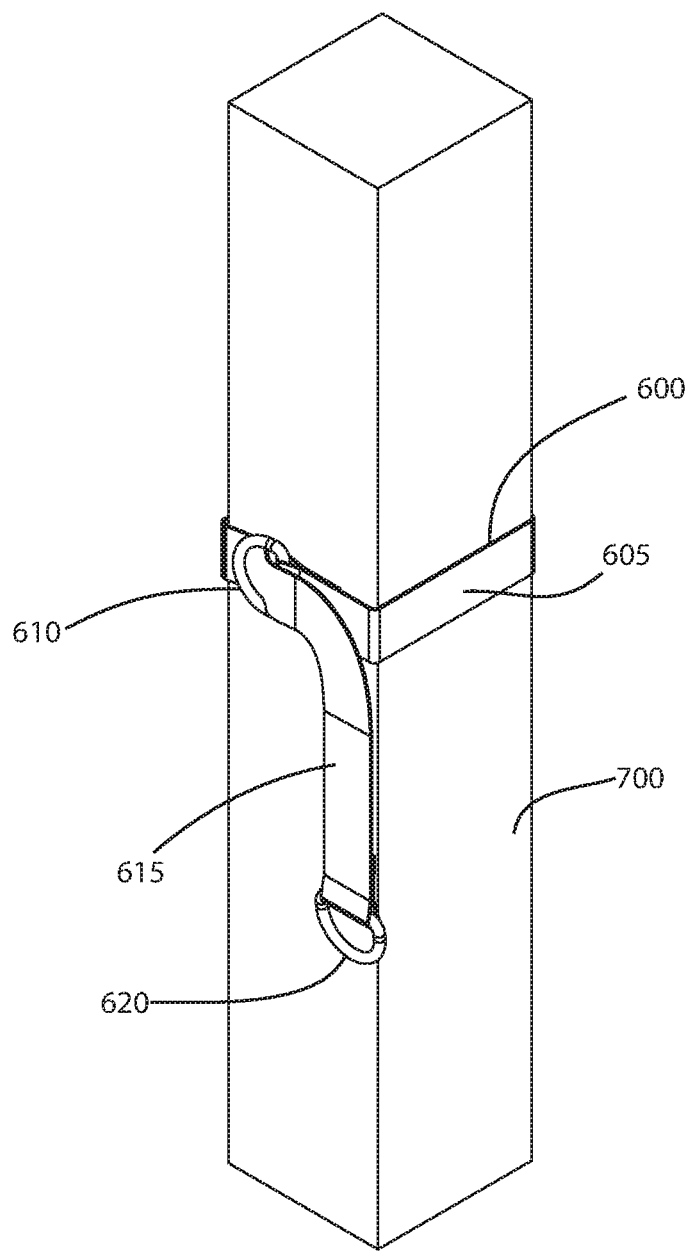
FIG. 10 is a top perspective view of a leg anchor, in use, for a traction device according to principles of the invention.

While the illustrated door 400 includes three hinges 410, 415, 420 with the anchor 300 above the intermediate hinge 415, the invention is not limited to such a configuration. Rather, the invention may be used with doors having fewer or more hinges. Even without an intermediate hinge 415, the anchor 300 may be frictionally secured (i.e., clamped) between the door 400 and frame 405 at a height above the bottom of the door. Structures other than a door may be used for anchoring in accordance with principles of the invention, as discussed in more detail below with reference to FIG. 10.

Figure 4:
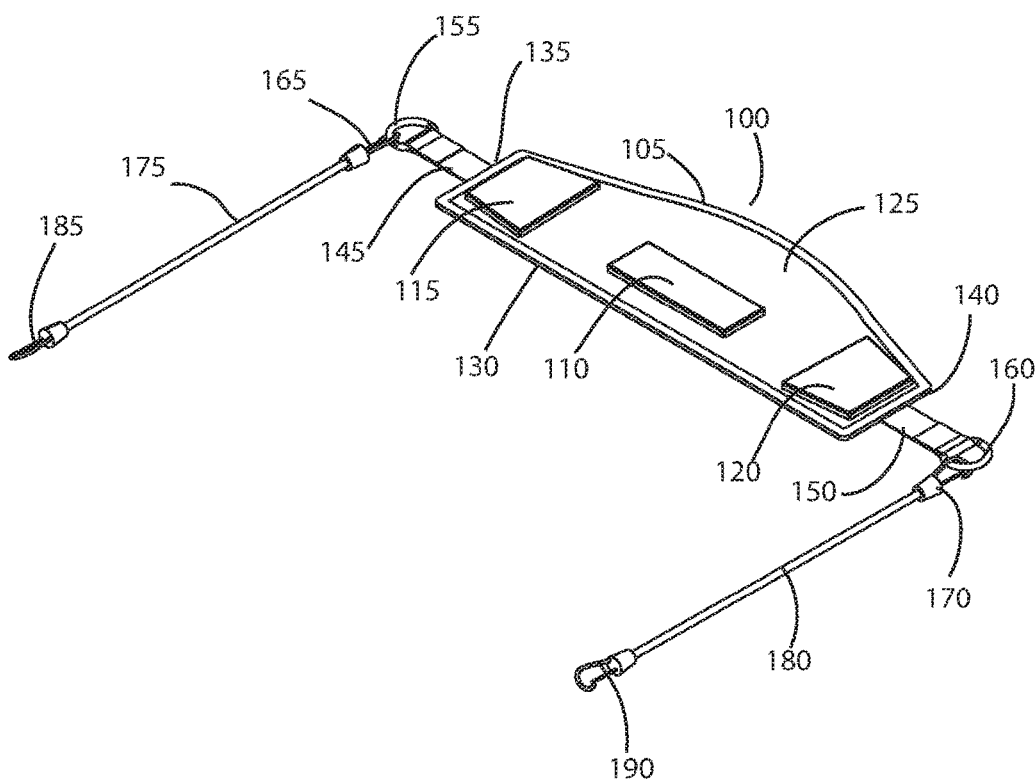
FIG. 4 is a top perspective view that conceptually illustrates a sling assembly for a traction device in use according to principles of the invention.
Figure 5:
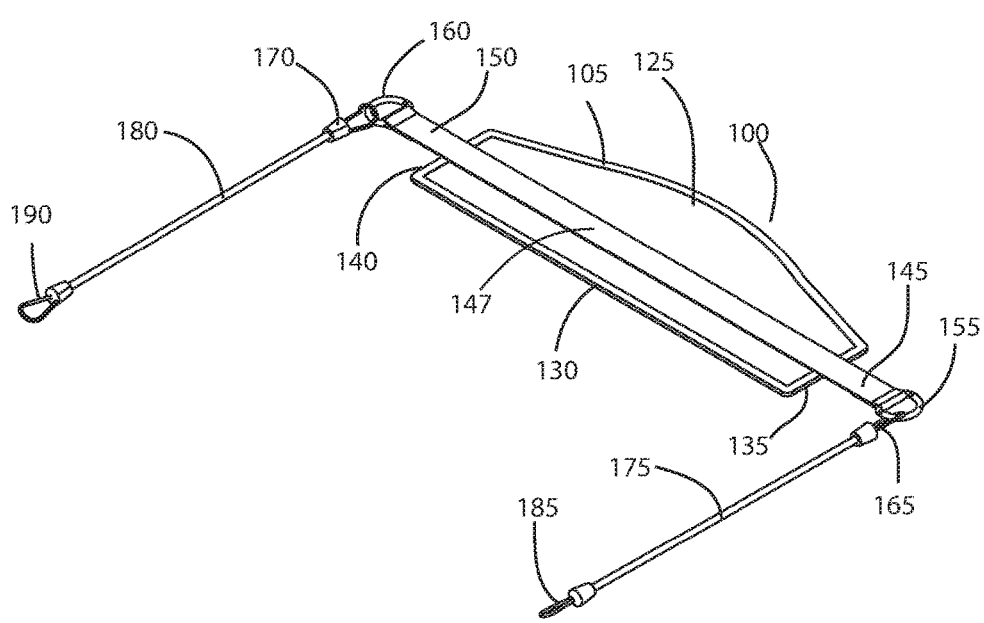
FIG. 5 is a bottom perspective view that conceptually illustrates a sling assembly for a traction device in use according to principles of the invention.

Referring now to FIGS. 4 and 5, the sling assembly 100 and shock cords 205, 210 are more clearly shown. Each shock cord 205, 210 includes an elastic cord 175, 180 composed of one or more elastic strands forming a core, covered in a woven sheath. While the sheath does not extend elastically, its strands spiral around the core so that a longitudinal pull causes it to squeeze the core, transmitting the core's elastic compression to the longitudinal extension of the sheath and cord. Elastic cords other than sheathed shock cords may be utilized without departing from the scope of the invention. Non limiting examples include elastic straps such as EPDM and natural rubber tarp straps equipped with S-hooks at each end.

The shock cords 205, 210 or other elastic cords exert a tension when stretched. The tensile force is preferably at least 5 lbs for cervical traction, more preferably 10 to 30 pounds, and up to 5% to 10% of the user's body weight. A plurality of (e.g., 2, 4, 6 or 8) shock cords may be used to achieve a desired tensile force. Additionally, tension is a function of the strain (i.e., ΔL/L, where L is the original length and ΔL is the elongation) of the shock cord or elastic cord, with tension increasing with increasing strain. Thus, tensile force may be adjusted by adjusting the strain.

Each shock cord 205, 210 includes a metal or plastic hook 165, 185 and 170, 190 attached to each end of the cord 205, 210. The hooks 165, 185 and 170, 190, may be opened or closed. Attachments other than hooks, such as shackles, carabiners and straps may be utilized, at either or both ends of each shock cord to guard against unintentional disengagement of the shock cord.

A pair of flexible strap ends 145, 150 extend from opposite side edges 135, 140 of the sling assembly. A nonlimiting example of a suitable flexible strap is nylon webbing. Attachments, such as D-rings 155, 160 are attached to the free ends of the strap ends 145, 150. Shock cords 205, 210 connect to the attachments, i.e., to the D-rings 155, 160. As shown in FIG. 5, the strap ends 145, 150 may be opposite ends of strap 147 that extends across the bottom of sling assembly 100. The strap 147 may be permanently or removably attached to the sling assembly, such as with stitching, hook and loop fasteners, or belt loops.

The base 125 of the sling assembly 100 includes a top edge 105 with an arched (convex) section, an opposite bottom edge 130, and opposite side edges 135, 140. The base 125 is substantially planar. It may be comprised of any flexible fabric, including natural or synthetic fiber fabrics, that is comfortable, strong and durable. Nylon webbing, ballistic nylon fabric, nylon pack cloth, nylon canvass are non-limiting examples.

A plurality of cushions 110, 115, and 120 are provided for comfort at all pressure points. While three cushions are illustrated, one large cushion or several separate cushions may be used. Base cushion 110 is positioned where the occipital bone portion of the user's head will be located during normal use. Side cushions 115, 120 are positioned to cushion the sides of a user's head, below the ears, where the lambdoid suture and lateral portions of the parietal bones of the user's head are located.

Figure 6:
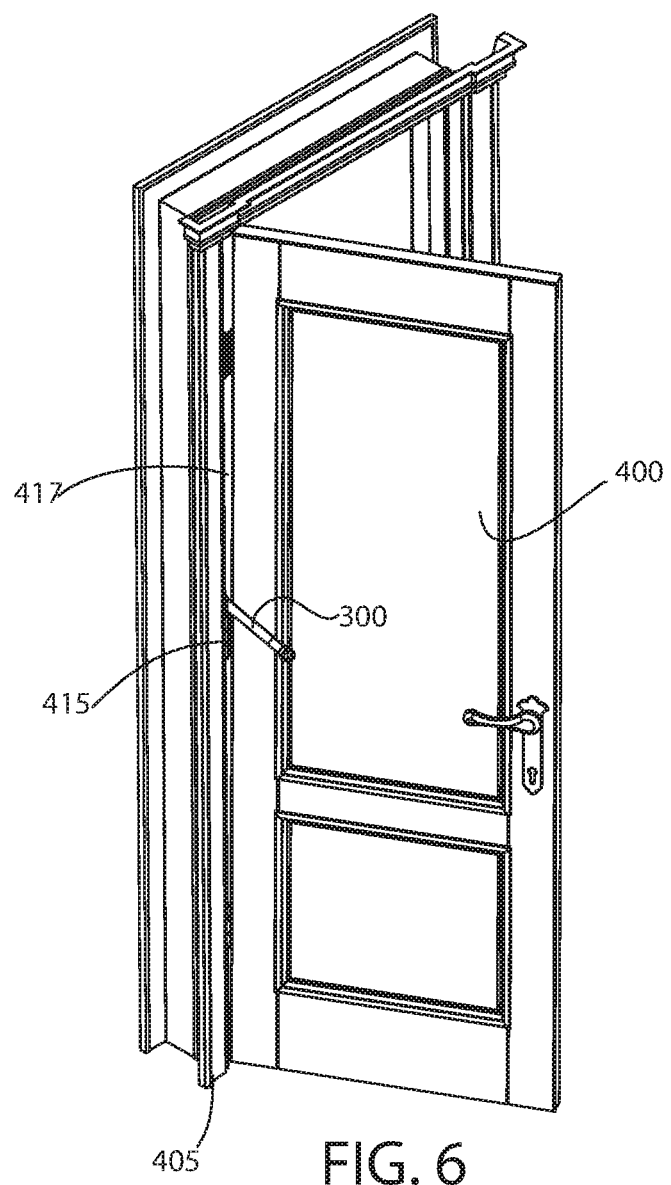
FIG. 6 is a top perspective view that conceptually illustrates a door anchor, in use, for a traction device according to principles of the invention.

In an exemplary implementation, an anchor is attached to a door 400, actually between the hinged side of the door 400 and the door frame 405. When the door is opened as shown in FIG. 6, an anchor tab 315 of an anchor 300 is slipped through the space 417 exposed between the hinged edge of the door 400 and the door frame 405, at a desired height. When the door 400 is closed, the space 417 is reduced or eliminated to prevent dislodging the anchor tab 315.

With reference to FIGS. 7 through 9 an exemplary door anchor 300 for a traction device according to principles of the invention is conceptually illustrated. The anchor includes a flexible strap 310 (e.g., nylon webbing) with an attachment (e.g., D-ring) 305 at one end, and an anchor tab 315 at the opposite end. The anchor tab 315 is sized to fit through the space exposed between the hinged edge of a door and a door frame, when the door is open. However, the anchor is thick enough to resist withdrawal through the space when the door is closed. The anchor tab 315 is firmly attached to the end of the strap 310 to prevent disconnection. The anchor tab may comprise a plastic tab of 0.1 to 0.5 inches in thickness, or folded and sewn lawyers of webbing with stitched seams, or other rigid structures including hardwood, metal and composite prismatic polyhedron shaped tab-like structures of appropriate size. The strap 310 is thin enough to allow closure of the door with the strap 310 between the hinged edge and frame of the door. While a D-ring 305 is illustrated for attachment to shock cord 205, 210, other attachments such as carabiners, shackles, loops, spring clips, buckles and the like may be utilized within the scope of the invention.

Attachment to a door is preferred, as doors are ubiquitous. However, an anchor may be attached to other structures such as a table leg 700 as conceptually illustrated in FIG. 10. In this embodiment, the anchor 600 is comprised of a strap 605 with D-rings 610, 620 at each end, and a segment of the strap 615 threaded through one of the D-rings 610 to define a slip knot or noose surrounding the periphery of the leg 700 at a certain height. In such an implementation, one D-ring 610 may also serve as an anchor tab for use with a door.

FIG. 11 is a plan view of an alternative anchor 800 for a traction device according to principles of the invention. FIG. 12 is a top perspective view of the alternative anchor 800 illustrated in FIG. 11, and FIG. 13 is a side view of the alternative anchor 800 illustrated in FIG. 11. As shown in FIGS. 11-13, the alternative anchor 800 includes a strap 810 with an attachment (e.g., D-ring) 805 at one end of the strap 810. The other end of the strap 810 forms a loop 820 defined by a portion of the strap 810 folded over and secured to itself at anchor tab 815. As shown, the anchor tab 815 is thicker than other portions of the strap 810 due to the overlay of multiple layers of the strap 810.

Figure 14:
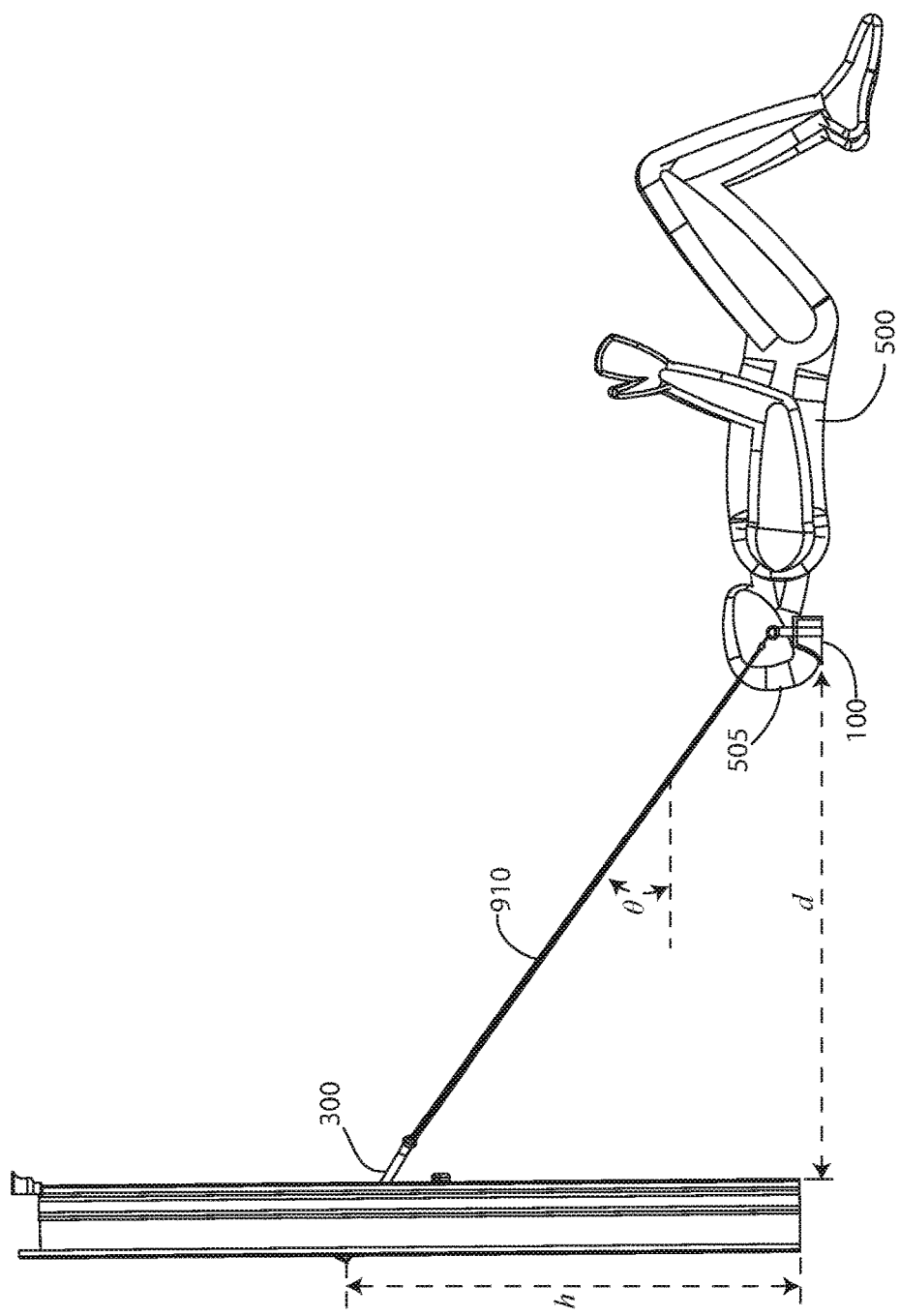
FIG. 14 is a side view that conceptually illustrates a traction device in use according to principles of the invention.
Figure 15:
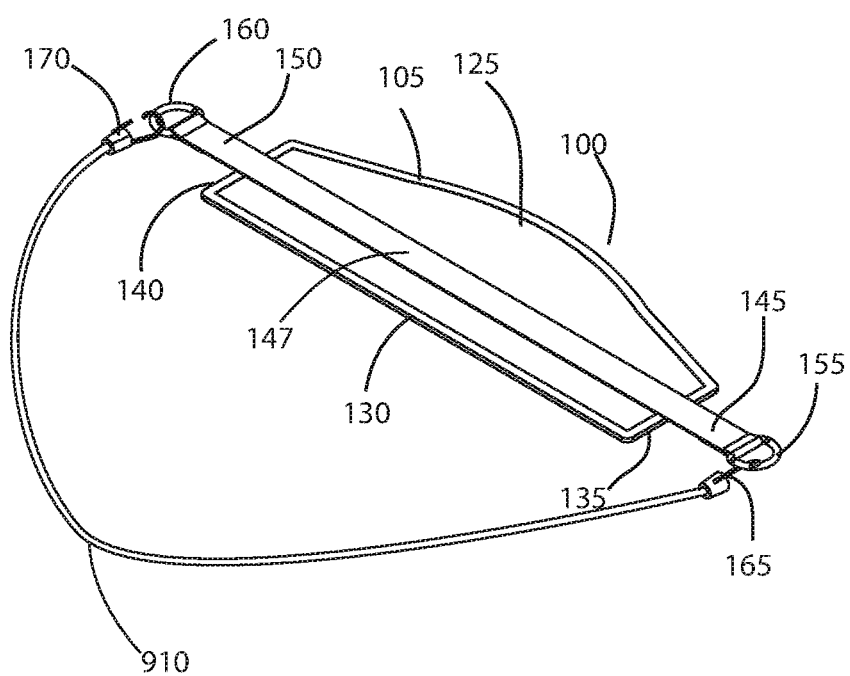
FIG. 15 is a bottom perspective view that conceptually illustrates a sling assembly for a traction device in use according to principles of the invention.

FIG. 14 is a side view that conceptually illustrates the traction device of FIG. 15 in use according to principles of the invention. As shown in FIG. 14, the sling assembly 100 cradles a user's 500 head 505 when the cord 910 is attached to the sling assembly 100 and to a door anchor 300. FIG. 15 illustrates a bottom perspective view that conceptually illustrates the sling assembly 100 associated with cord 910. As shown, the cord 910 includes a first end 165 with a hook that attaches to a D-ring 155 associated with one end 145 of the strap 147. The cord 910 also includes a second end 170 with a hook that attaches to a D-ring 160 associated with the other end 150 of the strap 147.

While an exemplary embodiment of the invention has been described, it should be apparent that modifications and variations thereto are possible, all of which fall within the true spirit and scope of the invention. With respect to the above description then, it is to be realized that the optimum relationships for the components and steps of the invention, including variations in order, form, content, function and manner of operation, are deemed readily apparent and obvious to one skilled in the art, and all equivalent relationships to those illustrated in the drawings and described in the specification are intended to be encompassed by the present invention. The above description and drawings are illustrative of modifications that can be made without departing from the present invention, the scope of which is to be limited only by the following claims. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents are intended to fall within the scope of the invention as claimed.

What is claimed is:

1. A portable for providing cervical traction, the portable traction device comprising:
 a sling assembly, comprising:
  a sling comprising flexible material and having a first side, a second side opposite the first side, a superior edge, and an inferior edge, the sling being elongated and sized to cradle and engage an occipital bone portion of a user's head via at least a frictional portion of the sling disposed between the superior edge and the inferior edge of the sling when the first side extends to a first side of the user's head and the second side extends to a second side of the user's head;
  a base cushion attached to the sling between the superior edge and the inferior edge and approximately centered between the first and second sides of the sling;
  a first side cushion disposed between the base cushion and the and the first side of the sling;
  a second side cushion disposed between the base cushion and the second side of the sling; and
  a pair of side attachments comprising a first side attachment extending from the first side of the sling and a second side attachment extending from the second side of the sling;
 flexible elastic tethers operable to selectively attach to the pair of side attachments via first ends of the flexible elastic tethers; and
 an anchor operable to selectively attach to the sling and to an anchoring object, wherein the anchor comprises:
  an anchor tab;
  an anchor connector operable to selectively attach to second ends of the flexible elastic tethers; and
  an anchor strap disposed between and connecting the anchor tab and the anchor connector.

2. The portable traction device of claim 1, wherein the pair of side attachments each comprise at least one of a shackle, a ring, a hook or a clip.

3. The portable traction device of claim 2, wherein the pair of side attachments each comprise the ring and the first ends of the flexible elastic tethers each comprise a complementary hook or clip configured to selectively attach to the ring.

4. The portable traction device of claim 3, wherein the flexible elastic tethers are strained and at an acute angle relative to a floor while the portable traction device is in use, the strained flexible elastic tethers producing a tensile force in a direction of the acute angle.

5. The portable traction device of claim 1, wherein the sling comprises an inner first layer, a second layer, and an exterior third layer, the inner first layer and the exterior third layer comprising the flexible material and the second layer comprising a flexible cushioning material disposed between the inner first layer and the exterior third layer.

6. The portable traction device of claim 1, wherein the anchor tab is sized and shaped (i) to fit through a space exposed between a hinged edge of a door and a door frame when the door is open and (ii) to resist withdrawal through the space when the door is closed.

7. A method of applying cervical traction, comprising:
 providing the portable traction device of claim 1;
 attaching the anchor to the anchoring object, at a height above a floor; stretching the pair of flexible elastic tethers at an acute angle relative to the floor to produce a tensile force including a vector component parallel to the floor and towards the anchor, and a vector component perpendicular to the floor and upward; and
 attaching the anchor to the anchoring object, at a height above the floor; stretching the flexible elastic tethers at an acute angle relative to the floor to produce a tensile force including a vector component parallel to the floor and towards the anchor, and a vector component perpendicular to the floor and upward; and
 cradling a head of a supine user with the while the flexible elastic tethers are stretched.

8. The method of claim 7, wherein the tensile force produced by stretching the flexible elastic tethers is at least five pounds.

9. The method of claim 8, wherein the head of the supine user is spaced apart from and aimed towards the anchoring object, and feet of the supine user are aimed away from the anchoring object.

10. The portable traction device of claim 1, wherein each of the flexible elastic tethers comprises a shock cord.

11. The portable traction device of claim 10, the first ends of the flexible elastic tethers each comprise a hook or a clip configured to selectively attach to one or more of the first or second side attachments.

12. The portable traction device of claim 11, wherein each of the pair of side attachments comprise a ring.

13. The portable traction device of claim 11, wherein each of the pair of side attachments comprise a carabiner.

14. A portable traction device for providing cervical traction, the portable traction device comprising:
 a sling comprising flexible material and having a first side, a second side opposite the first side, a superior edge, and an inferior edge, the sling being elongated and sized to cradle and engage an occipital bone portion of a user's head via at least a frictional portion of the sling disposed between the superior edge and the inferior edge of the sling when the first side extends to a first side of the user's head and the second side extends to a second side of the user's head;
 a pair of side attachments comprising a first side attachment extending from the first side of the sling and a second side attachment extending from the second side of the sling;
 flexible elastic tethers comprising first ends and second ends, the first ends being associated with the pair of side attachments; and
 an anchor operable for selective attachment to an anchoring object at a height above a floor while the portable traction device is in use, the second ends of the flexible elastic tethers being associated with the anchor,
 wherein the flexible elastic tethers are strained and at an acute angle relative to the floor while the portable traction device is in use, the strained flexible elastic tethers producing a tensile force in a direction of the acute angle, and
 wherein the anchor comprises:
  an anchor tab;
  an anchor connector operable to selectively attach to second ends of the flexible elastic tethers; and
  an anchor strap disposed between and connecting the anchor tab and the anchor connector.

15. The portable traction device of claim 14, wherein the sling comprises an inner first layer, a second layer, and an exterior third layer, the inner first layer and the exterior third layer comprising flexible fabric and the second layer comprising a flexible cushioning material disposed between the inner first layer and the exterior third layer.

16. The portable traction device of claim 14, further comprising at least one cushion, the at least one cushion including a base cushion attached to the sling between the superior edge and the inferior edge and approximately centered between the first side of the sling and the second side of the sling.

17. The portable traction device of claim 16, wherein the at least one cushion further comprises a first side cushion and a second side cushion, the first side cushion being disposed between the base cushion and the first side of the sling, and the second side cushion being disposed between the base cushion and the second side of the sling.

18. The portable traction device of claim 14, wherein the tensile force is greater than 5 pounds.

\* \* \* \* \*

UNITED STATES PATENT AND TRADEMARK OFFICE
CERTIFICATE OF CORRECTION

PATENT NO. : 10,307,284 B2
APPLICATION NO. : 16/008247
DATED : June 4, 2019
INVENTOR(S) : Steven Sudell Page 1 of 1

It is certified that error appears in the above-identified patent and that said Letters Patent is hereby corrected as shown below:

On the Title Page

Item (57), Abstract, Lines 3-4, change "shock cords opposite shockcords are anchored is anchored to a structure" to —shock cords are anchored to a structure—

In the Specification

Column 1
Line 37, change "individual apply" to —individual can apply—

In the Claims

Column 7
Line 2, Claim 1 change "portable for" to —A portable traction device for—
Line 21, Claim 1 remove second instance of "and the"

Column 8
Line 9, Claim 7 change "with the while" to —with the sling assembly while—
Line 22, Claim 11 change "comprise" to —comprising—

Signed and Sealed this
Twenty-third Day of June, 2020

Andrei Iancu
*Director of the United States Patent and Trademark Office*